United States Patent
Dalton et al.

(10) Patent No.: US 8,489,195 B2
(45) Date of Patent: Jul. 16, 2013

(54) ARRANGEMENT FOR THE FIXATION OF AN IMPLANTABLE MEDICAL DEVICE

(75) Inventors: James William Leith Dalton, Beecroft (AU); Peter Gibson, South Coogee (AU); Charles Roger Aaron Leigh, East Ryde (AU); Mark von Huben, Waverton (AU)

(73) Assignee: Cochlear Limited, Macquarie University, NSW (AU)

( * ) Notice: Subject to any disclaimer, the term of this patent is extended or adjusted under 35 U.S.C. 154(b) by 912 days.

(21) Appl. No.: 12/093,402

(22) PCT Filed: Nov. 2, 2006

(86) PCT No.: PCT/AU2006/001632
§ 371 (c)(1),
(2), (4) Date: Oct. 17, 2008

(87) PCT Pub. No.: WO2007/053882
PCT Pub. Date: May 18, 2007

(65) Prior Publication Data
US 2009/0099658 A1   Apr. 16, 2009

(30) Foreign Application Priority Data

Nov. 10, 2005  (AU) ................................ 2005906228

(51) Int. Cl.
*A61N 1/00*  (2006.01)
(52) U.S. Cl.
USPC .............................. 607/57; 607/116; 606/300

(58) Field of Classification Search
USPC ...... 607/55–57, 109, 116, 136–137; 600/372, 600/377–379; 606/300; 623/10, 11.11
See application file for complete search history.

(56) References Cited

U.S. PATENT DOCUMENTS

| | | |
|---|---|---|
| 2,487,038 A | 11/1949 | Baum |
| 2,641,328 A | 6/1953 | Beaudry |
| 4,055,233 A | 10/1977 | Huntress |
| 4,333,469 A | 6/1982 | Jeffcoat et al. |
| 4,488,561 A | 12/1984 | Doring |
| 4,532,930 A | 8/1985 | Crosby et al. |
| 4,612,915 A | 9/1986 | Hough et al. |
| 4,744,792 A | 5/1988 | Sander et al. |
| 4,904,233 A | 2/1990 | Hakansson et al. |
| 4,986,831 A | 1/1991 | King et al. |

(Continued)

FOREIGN PATENT DOCUMENTS

| | | |
|---|---|---|
| RU | 2282426 | 8/2006 |
| WO | 8300999 | 3/1983 |

(Continued)

OTHER PUBLICATIONS

International Search Report issued by the International Searching Authority in connection with PCT application No. PCT/AU2000/000936, dated Oct. 10, 2000 (3 pages).

(Continued)

*Primary Examiner* — Mark W Bockelman
(74) *Attorney, Agent, or Firm* — Kilpatrick, Townsend & Stockton, LLP.

(57) ABSTRACT

A medical implant, such as a cochlear implant, comprising a fixating point which is located remotely from the medical implant. This arrangement can reduce the risk of post operative infection in a patient in which the medical implant is implanted.

17 Claims, 9 Drawing Sheets

U.S. PATENT DOCUMENTS

| | | | |
|---|---|---|---|
| 5,176,620 | A | 1/1993 | Gilman |
| 5,277,694 | A | 1/1994 | Leysieffer et al. |
| 5,282,253 | A | 1/1994 | Konomi |
| 5,443,493 | A | 8/1995 | Byers et al. |
| 5,558,618 | A | 9/1996 | Maniglia |
| 5,572,594 | A | 11/1996 | Devoe et al. |
| 5,738,521 | A | 4/1998 | Dugot |
| 5,814,095 | A | 9/1998 | Muller et al. |
| 5,881,158 | A | 3/1999 | Lesinski et al. |
| 5,906,635 | A | 5/1999 | Maniglia |
| 5,999,632 | A | 12/1999 | Leysieffer et al. |
| 6,042,380 | A | 3/2000 | De Rowe |
| 6,070,105 | A | 5/2000 | Kuzma |
| 6,125,302 | A | 9/2000 | Kuzma |
| 6,132,384 | A | 10/2000 | Christopherson et al. |
| 6,161,046 | A * | 12/2000 | Maniglia et al. |
| 6,381,336 | B1 | 4/2002 | Lesinski et al. |
| 6,427,086 | B1 | 7/2002 | Fischell et al. |
| 6,516,228 | B1 | 2/2003 | Berrang et al. |
| 6,537,200 | B2 | 3/2003 | Leysieffer et al. |
| 6,565,503 | B2 | 5/2003 | Leysieffer et al. |
| 6,575,894 | B2 | 6/2003 | Leysieffer et al. |
| 6,697,674 | B2 | 2/2004 | Leysieffer |
| 6,730,015 | B2 | 5/2004 | Schugt et al. |
| 6,840,919 | B1 | 1/2005 | Hakansson |
| 7,043,040 | B2 | 5/2006 | Westerkull |
| 2002/0019669 | A1 | 2/2002 | Berrang et al. |
| 2004/0260361 | A1 | 12/2004 | Gibson |
| 2006/0116743 | A1 | 6/2006 | Gibson et al. |

FOREIGN PATENT DOCUMENTS

| | | |
|---|---|---|
| WO | 9429932 | 12/1994 |
| WO | 9705673 | 2/1997 |
| WO | WO 97/36457 A1 | 10/1997 |
| WO | 9906108 | 2/1999 |
| WO | 0071063 | 11/2000 |
| WO | 0110369 | 2/2001 |
| WO | 03070133 | 8/2003 |
| WO | 03092326 | 11/2003 |
| WO | 2004014269 | 2/2004 |
| WO | 2004014270 | 2/2004 |
| WO | 2007053882 | 5/2007 |

OTHER PUBLICATIONS

International Preliminary Examination Report issued by the International Preliminary Examining Authority in connection with PCT application No. PCT/AU2000/000936, dated Jun. 8, 2001 (3 pages).

International Search Report issued by the International Searching Authority in connection with PCT application No. PCT/AU2003/000229, dated May 5, 2003 (5 pages).

Written Opinion issued by the International Preliminary Examining Authority in connection with PCT application No. PCT/AU2003/000229, dated Jun. 30, 2003 (6 pages).

International Preliminary Examination Report issued by the International Preliminary Examining Authority in connection with PCT application No. PCT/AU2003/000229, dated May 24, 2004 (6 pages).

Written Opinion issued by the International Preliminary Examining Authority in connection with PCT application No. PCT/AU2003/001004, dated Jan. 9, 2004 (3 pages).

International Search Report issued by the International Searching Authority in connection with PCT application No. PCT/AU2003/001004, dated Oct. 13, 2003 (2 pages).

International Preliminary Examination Report issued by the International Preliminary Examining Authority in connection with PCT application No. PCT/AU2003/001004, dated Nov. 22, 2004 (3 pages).

International Search Report issued by the International Searching Authority in connection with PCT application No. PCT/AU2003/001012, dated Oct. 13, 2003 (5 pages).

Written Opinion issued by the the International Preliminary Examining Authority in connection with PCT application No. PCT/AU2003/001012, dated Feb. 23, 2004 (3 pages).

International Preliminary Examination Report issued by the International Preliminary Examining Authority in connection with PCT application No. PCT/AU2003/001012, dated Nov. 23, 2004 (3 pages).

Written Opinion issued by the International Searching Authority in connection with PCT application No. PCT/AU2006/001632, dated Dec. 1, 2006 (5 pages).

International Preliminary Report on Patentability issued by The International Bureau of WIPO in connection with PCT application No. PCT/AU2006/001632, dated May 14, 2008 (6 pages).

Niznick, Gerald A., "Achieving Osseointegration in Soft Bone: The Search for Improved Results," pp. 27-32, Oral Health, Aug. 2000 (6 pages).

Gibson, Peter, "Mechanical Design for a Cochlear Implant," filed with the United States Patent and Trademark Office on Feb. 9, 2005, assigned U.S. Appl. No. 10/523,795, filed Jun. 30, 2005 (30 pages).

International Search Report. PCT/AU2006/001632. Mailed Dec. 1, 2006.

* cited by examiner

ARRANGEMENT FOR THE FIXATION OF AN IMPLANTABLE MEDICAL DEVICE

FIELD OF THE INVENTION

This invention relates to the fixation of implantable medical devices such as a cochlear implant, within a patient.

PRIORITY

This application claims priority from Australian Provisional Patent Application No. 2005906228 filed on 10 Nov. 2005. The entire content of this application is hereby incorporated by reference.

BACKGROUND OF THE INVENTION

Medical implants are used in many areas of medicine to enhance the length and/or quality of the life of the implant recipient. Such implants include pacemakers, controlled drug delivery implants and cochlear implants.

The insertion of such devices often requires surgery, and once in place, it is desirable to not have to replace the device, or if occasional replacement is necessary, the number of replacement procedures should be kept to a minimum.

One major factor in determining whether a patient must undergo surgery again is the secure fixation of the device within the patient. If the device has not been securely fixed in position, it may be necessary to repeat the procedure.

An improperly fixed device can result in less than optimal performance of the device, as well as severe medical consequences for the patient.

It is particularly important to have the device properly fixed in the early post operative stage, before fibrous tissue and bone has formed around the device to assist hi its retention.

The fixation of the implantable device often takes a significant proportion of the time of the surgery, and often necessitates the area around the implant site to be completely open, increasing the severity and risks of the surgery.

It is preferred to perform minimally invasive procedures to minimise the severity and risk of the surgery. One such procedure involves the use of a periosteal pocket, where a smaller incision is made, and the device is slid into the formed pocket between the bone and the tissue.

However, some types of medical implants do not lend themselves to this type of procedure. One such device is a cochlear implant, which is used to treat patients who suffer from hearing loss.

A cochlear implant allows for electrical stimulating signals to be applied directly to the auditory nerve fibres of the patient, allowing the brain to perceive a hearing sensation approximating the natural hearing sensation. These stimulating signals are applied by an array of electrodes implanted into the patient's cochlear.

The electrode array is connected to a stimulator unit which generates the electrical signals for delivery to the electrode array. The stimulator unit in turn is operationally connected to a signal processing unit which also contains a microphone for receiving audio signals from the environment, and for processing these signals to generate control signals for the stimulator.

The signal processing unit is in practice, located externally to the patient and the stimulator is implanted within the patient, usually near the mastoid on the patient's skull and underneath the surrounding tissue. The processor and stimulator may communicate by various wireless means including by a radio frequency link.

The implant procedure commonly involves removing some of the bone to form a well for receiving the stimulator to assist in the security of the fixation. Additional fixation is commonly used and is achieved using sutures or biocompatible screws.

Thus, fixating cochlear implants has traditionally required that the site of fixation be completely open to allow full and unrestricted access to the site. This requires a large opening to be formed, increasing the complexity of and the risk associated with the surgery as well as increasing the recovery time of the patient.

It is therefore an object of the present invention to provide a means of facilitating the fixation of a medical implant in a patient.

SUMMARY OF THE INVENTION

According to a first aspect of the present invention, there is provided a medical implant for implanting in a patient, the medical implant having a fixating point for fixating the medical implant to the patient, wherein the fixating point is disposed remotely from the medical implant.

In one form, the fixating point is provided on a fixating connector, connecting the fixating point to the medical implant.

In another form, the fixating connector is removably attachable to the medical implant.

In one form, the distance between the fixating point and the medical implant is variable.

In one form, the fixating connector is conformable.

In one form, the medical implant is a cochlear implant.

Optionally, the fixating connector at least partially houses at least a portion of a lead supporting an array of electrodes extending from the cochlear implant.

According to a second aspect of the invention, there is provided a fixating connector having a fixating point for fixating the fixating connector to a patient, and at least one connecting point for connecting the fixating connector to an implantable medical device.

In one form, the fixating connector is conformable.

In one form, the medical implant is a cochlear implant.

In one form, the fixating connector is able to act as a docking station for the medical implant.

According to a third aspect of the present invention, there is provided a medical implant having at least one connecting point for connection to a fixating connector according to the second aspect of the present invention. Preferably, the medical implant is a cochlear implant.

According to a fourth aspect of the present invention, there is provided a cochlear implant having a lead supporting an electrode array extending therefrom, the cochlear implant having an extension for at least partially housing at least a portion of the lead.

Optionally, the extension is removably attachable to the cochlear implant.

According to a fifth aspect of the present invention, there is provided a medical implant for implanting in a patient, the medical implant having at least one protrusion extending therefrom, for insertion into bone of the patient to thereby fixate the medical implant to the patient.

In one form, the at least one protrusion is angled so as to allow movement of the medical implant in one direction, but to impede movement in the opposite direction.

In one form, the at least one protrusion is collapsible.

In one form, the medical implant has a plurality of protrusions.

According to a sixth aspect of the present invention, there is provided a docking station for a medical implant, the docking station having at least one fixating point for fixating the docking station to a patient, and at least one medical implant engagement means for engaging the medical implant.

In one form, the medical implant is a cochlear implant.

In one form, the at least one engagement means is a clip.

BRIEF DESCRIPTION OF THE DRAWINGS

The invention will now be described with reference to the following drawings in which.

DETAILED DESCRIPTION OF THE PREFERRED EMBODIMENT

Figure 1:
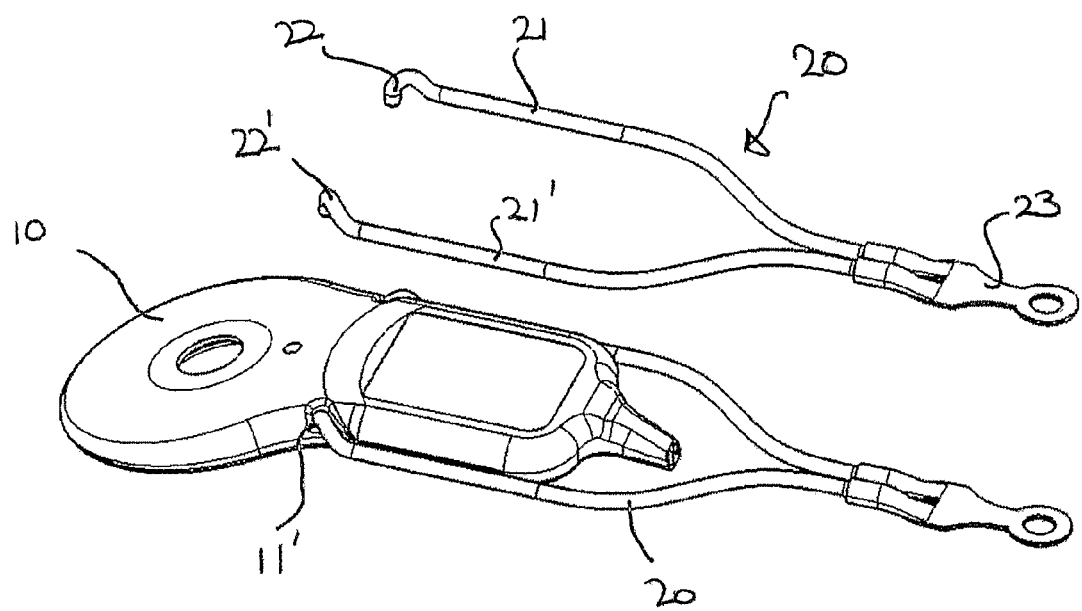
FIG. 1—shows a stimulator and fixation connector according to the present invention.

FIG. 1 shows an arrangement according to one aspect of the present invention. Illustrated is a fixation connector 20 provided in this case by a bracket having a fixating point 23 and two arms 21 and 21' terminating in hooks 22 and 22' respectively.

FIG. 1 also shows how bracket 20 connects to medical implant 10 (in this case, the stimulator unit of a cochlear implant). Stimulator unit 10 has holes 11 (not visible in FIG. 1) and 11' for receiving respective hooks 22 and 22' of the bracket 20. This provides a secure connection to bracket 20.

Stimulator unit 10 may be constructed such that its hermetically sealed casing may be extended to allow more space to provide receiving holes 11 and 11'. Alternatively, flanges may be added to provide location points.

According to an aspect of the present invention, the fixating point 23 of bracket 20 is located away from the stimulator unit 10. This allows stimulator 10 to be effectively fixated to the patient's skull by fixating the bracket 20 at the fixating point 23. It will be appreciated that the stimulator unit 10 can therefore be fixated without having to have access to the area around the stimulator unit 10. The fixation may be accomplished by simply fixating the bracket 20 at a single point and may be done via a much smaller incision.

Bracket 20 may be made from any suitable biocompatible material such as stainless steel, titanium, ceramic or polymeric material, or a combination of these materials as would be understood by the person skilled in the art. It will be appreciated that the choice of a suitable rigid material allows for the bracket to also form a handle with which to steer the implant into position, for example into a periosteal pocket.

Where the stimulator unit 10 is low in profile, bracket 20 enables fixation of the device without the need to drill the skull as is currently often required. This is particularly advantageous for patients with thin skulls such as infants. In these cases, drilling of the skull often results in complete removal of the bone down to the dura mater.

Nevertheless, bracket 20 is also removable to allow the stimulator unit 20 to be used in a more traditional procedure where a well may need to be formed in the skull and the bracket may not be needed and/or may be in the way. Removal may be before implantation or after placement of the implant, in which case the steering feature of the bracket can still be used.

Alternatively, if a well is used, the arms 21 of bracket 20 may be bent or conformed to accommodate the vertical displacement of the stimulator unit 10.

It will be appreciated that the invention also provides for flexibility in that it is applicable to, and allows, a range of different surgical techniques and is not limited to the particular ones described herein.

Figure 2:
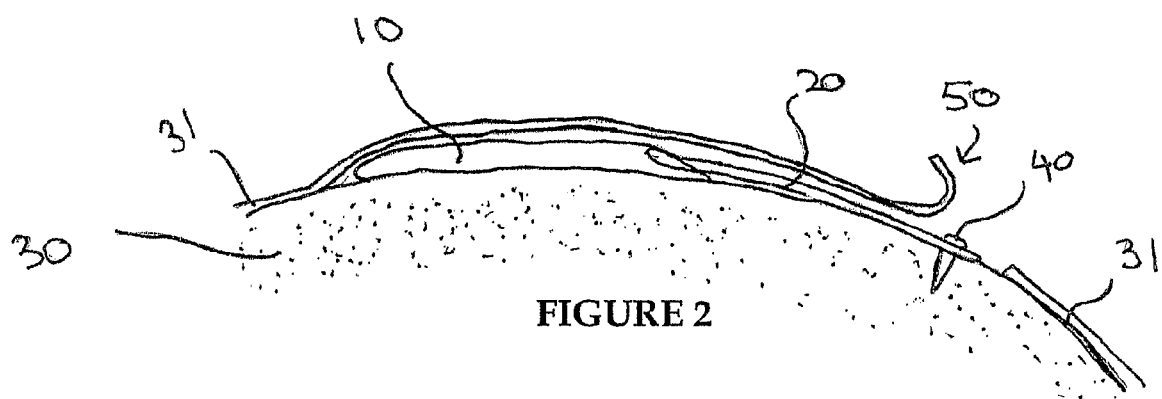
FIG. 2—shows the arrangement of FIG. 1 fixed to a patient's skull.

An illustration of the arrangement being put in place on the skull of a patient is shown in FIG. 2, in which a portion of the skull 30 is exposed by incision 50 and the stimulator unit 10 is slid between the skull 30 and scalp tissue 31 in a periosteal pocket.

The provision of bracket 20 allows the stimulator unit 10 to be pushed into the pocket and can also act as a handle to guide and place the stimulator unit 10 into a desired position, in the periosteal pocket. Once stimulator unit 10 is properly located, it can be fixated in place by fixating bracket 20 at the fixating point by means of biocompatible bone screw 40. Of course, any other means of fixation may be used as understood by the person skilled in the art. Once affixed, the bracket 20 prevents rotation and translation of the stimulator unit 10.

It will be appreciated that this arrangement allows for fixation of the stimulator unit 10 by minimally invasive techniques, thereby reducing the complexity and potential risk of the procedure. Furthermore, by allowing stimulator unit 10 to be placed away from the wound, the risk of postoperative infection is reduced.

Figure 3:
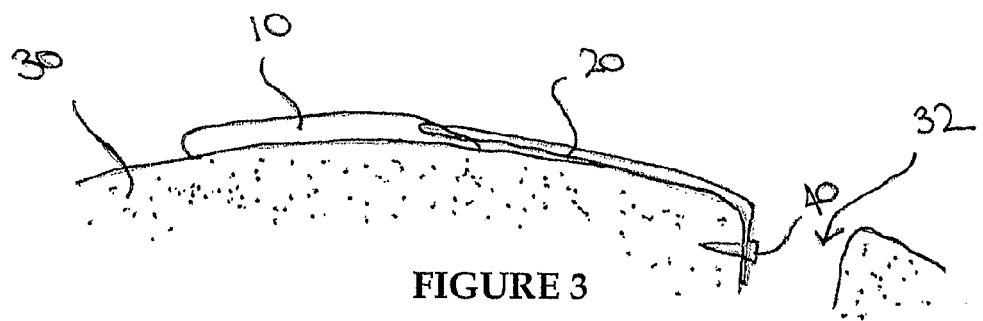
FIG. 3—shows an alternative form of fixing the arrangement of FIG. 1 to the patient's skull.

The plane of the bone screw 40 may be either lateral as shown in FIG. 2, or sagittal, as shown in FIG. 3. Arms 21, 21' of bracket 20 may be bent into a suitable position to allow the bracket 20 to be partially located in a depression or even a hole, such as the mastoid opening 32 as shown in FIG. 3. This allows fixation to be done on patients with thin skulls, such as children, which could not properly support a lateral fixation. The scalp tissue 31 of FIG. 2 has been omitted in FIG. 3 for clarity.

Figure 4:
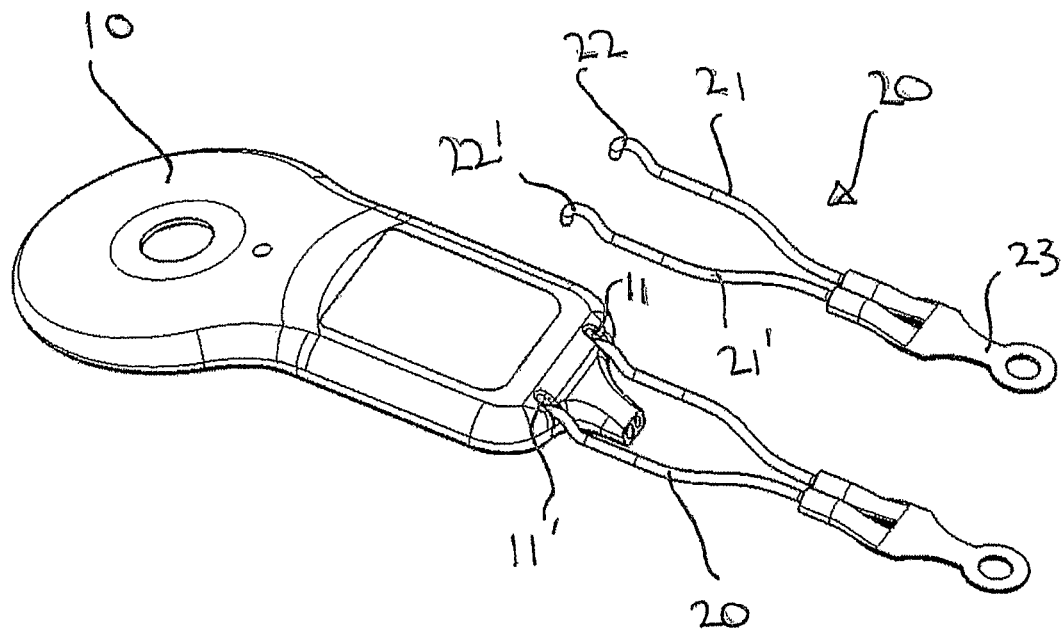
FIG. 4—shows an alternative form of the arrangement of FIG. 1.

FIG. 4 shows an alternative shape of bracket 20 with a different connection arrangement with stimulator unit 10. In this arrangement, hooks 22 and 22' are bent downwards so as to be able to be "dropped in" to receiving holes 11 and 11' formed in the casing of stimulator unit 10.

Figure 5:
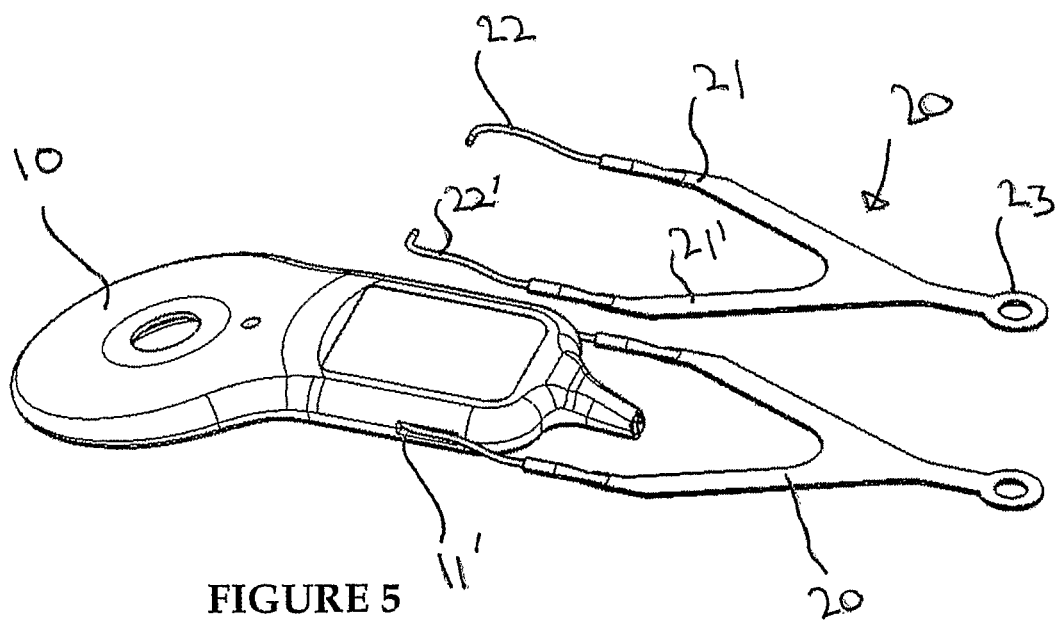
FIG. 5—shows a further alternative form of the arrangement of FIG. 1.

Alternatively, the connection between bracket 20 and stimulator unit 10 may be accomplished by providing holes 11 (not visible in this view) and 11' as shown in FIG. 5. In this arrangement, hooks 22 and 22' are turned inwards to clasp stimulator unit 10 there between.

In yet a further alternative (see FIG. 6), bracket 20 may be formed from a flat sheet of material with hooks 22, 22' being in the form of tabs. Arms 21, 21' are twisted so that tabs 22, 22' may be located in corresponding slots 11 (not visible in FIG. 6), 11' formed in the casing of stimulator unit 10. The tab/slot connection shown in FIG. 6 provides a very robust connection.

Figure 6:
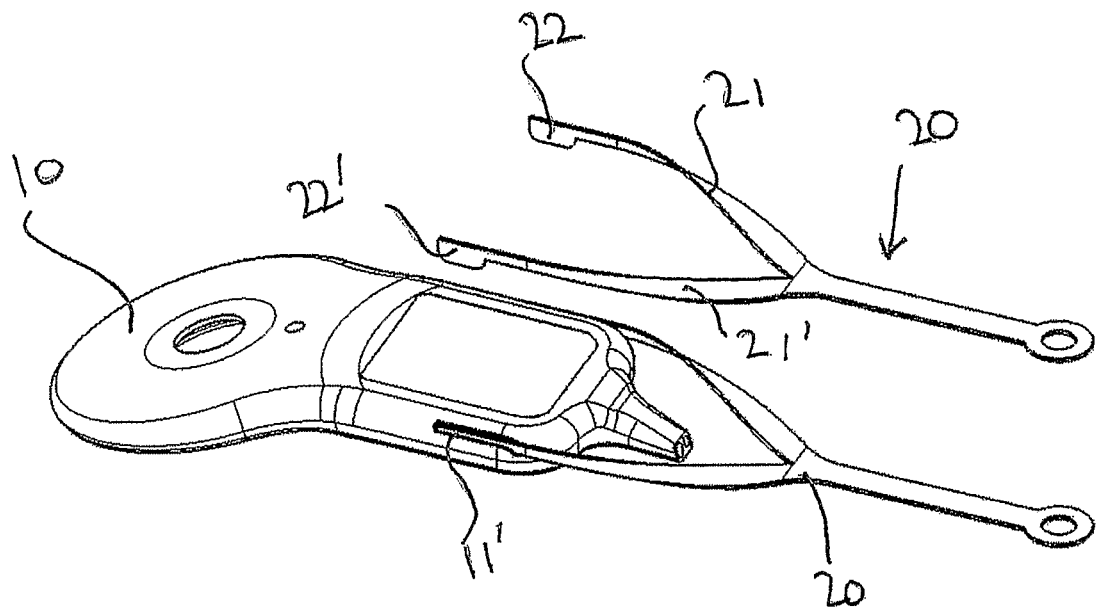
FIG. 6—shows yet a further alternative form of the arrangement of FIG. 1.
Figure 7:
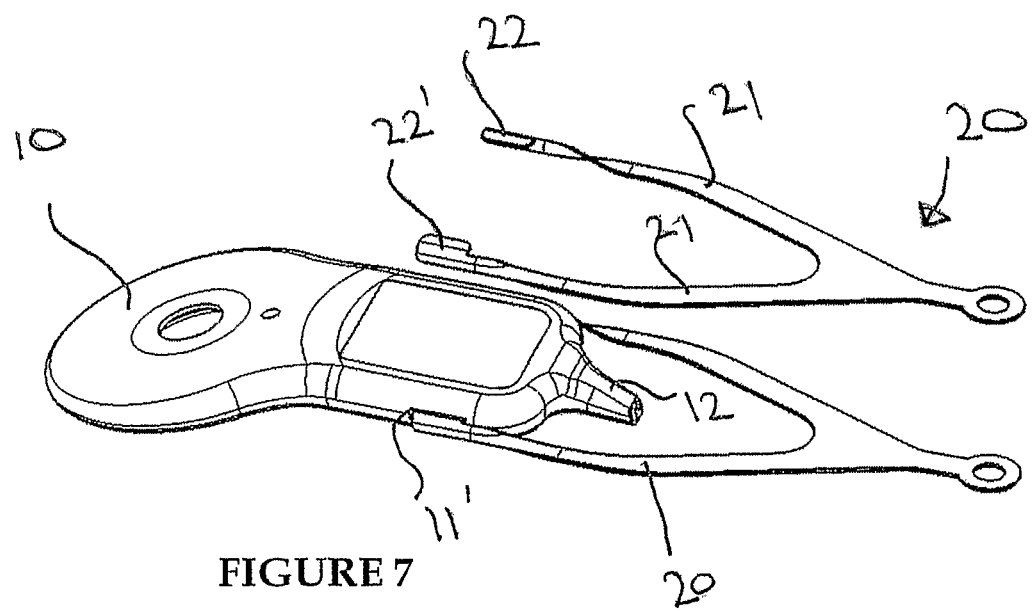
FIG. 7—shows yet a further alternative form of the arrangement of FIG. 1.

FIG. 7 shows a variation of the arrangement of FIG. 6 in which tabs 22, 22' are disposed horizontally and inwardly, to be received in corresponding slots 11 (not visible in FIG. 7), 11' in the side of stimulator unit 10. This configuration provides for a bracket 20 having a reduced profile.

An alternative of this form (or indeed any other form) could equally have protrusions extending from the casing of stimulator unit 10 to be received by corresponding recesses in hooks 22, 22'.

Figure 8:
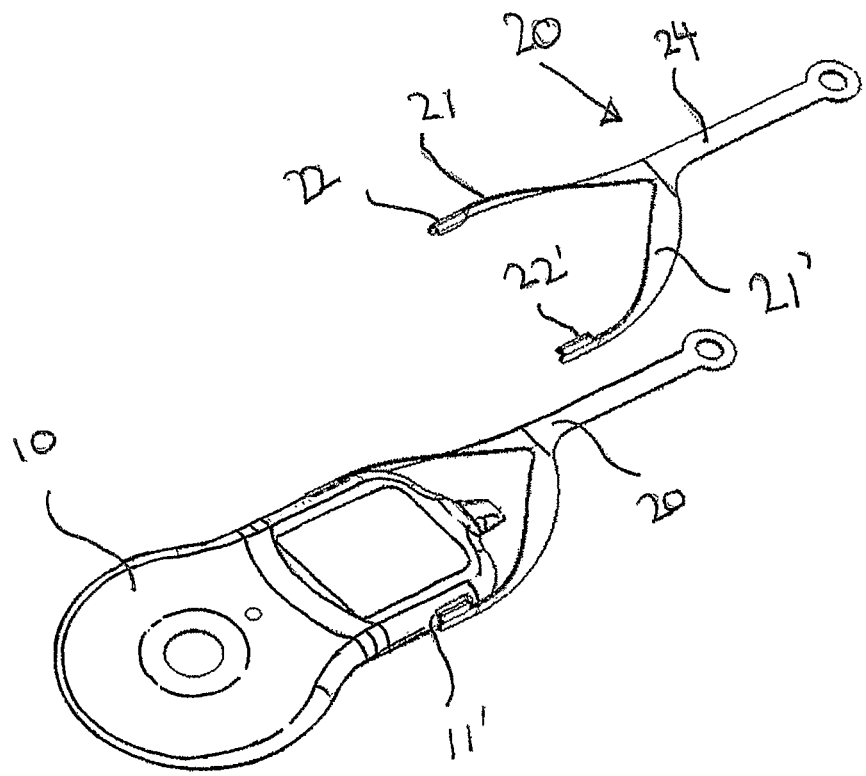
FIG. 8—shows yet a further alternative form of the arrangement of FIG. 1.

FIG. 8 shows a variation of the arrangement of FIG. 7, in which the shank 24 of the bracket 20 may also be offset from the centreline of the stimulator unit to provide a more favourable location point and to reduce the interference with the electrode array (not shown) extending from end 12 of the stimulator unit 10.

Figure 9:
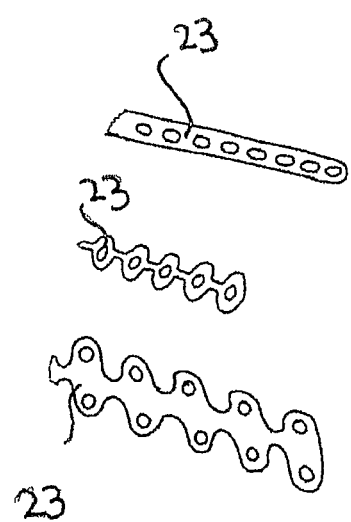
FIGS. 9A to 9C—are close up views of various forms of connection adjusting means.

FIG. 9 shows a number of alternative configurations for fixation point 23 of bracket 20. These configurations allow for tailoring of the proximity of the stimulator unit 20 to the location of fixation by providing a plurality of fixating points, which the surgeon can select as the desired fixating point for fixating the stimulator unit 10 to the patient. This effectively allows control over the distance of the stimulator unit 10 to the point of incision. If the surgeon selects a hole closer to the stimulator unit 10, then the excess material can be cut off.

It is also conceivable that the distance between the location of fixation and the stimulator unit 10 may also be varied by the provision of a plurality of hooks 22, 22' or holes on arms 21, 21', or equally a plurality of holes or protrusions 11, 11' on the stimulator unit 10.

Figure 10A:
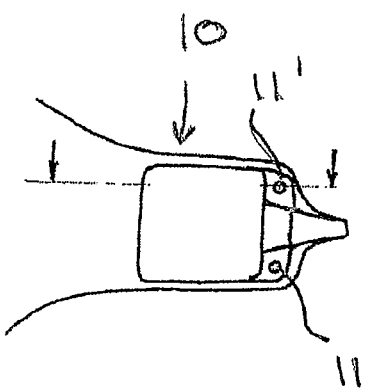
FIG. 10A—is a plan view of a portion of a stimulator that is modified to be used with the present invention.
Figure 10B:
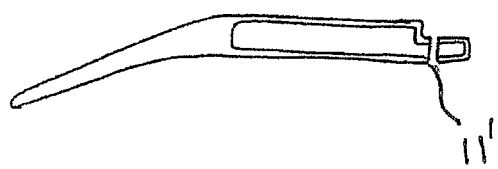
FIG. 10B—is a side view of the stimulator of FIG. 10A.

FIG. 10A shows a top view of the stimulator unit 10 casing in which holes 11, 11' have been formed to receive hooks 22, 22' of the bracket 20 respectively. FIG. 10B is a side view of the unit in FIG. 10A. This shows the casing designed with some excess material to provide a location for the holes.

If the stimulator unit 10 casing is electrically live, it is desirable to insulate the stimulator from the bracket 20. This could be accomplished in a number of ways including making the bracket 20, or at least the hooks 22, 22' from a biocompatible insulating material such as PEEK. Insulation of the stimulator unit 10 is generally accomplished by overmoulding with silicone rubber.

Figure 11:
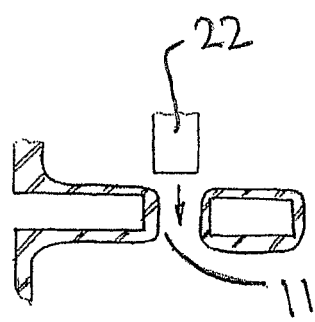
FIG. 11—is a cross-sectional view of the stimulator of FIG. 10B.

Alternatively, the holes 11, 11' in the stimulator unit casing may be insulated as shown in FIG. 11.

Figure 12:
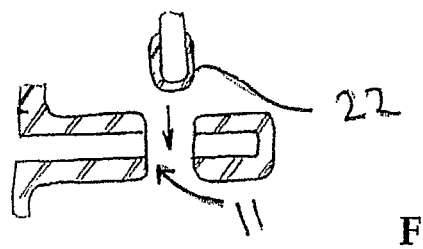
FIG. 12—is a cross-sectional view of an alternative of the arrangement of FIG. 11.

If the holes are drilled post manufacture, leaving exposed conductive material within the holes, the hooks themselves could just be coated with the insulating material as depicted in FIG. 12.

The addition of an insulating coating to either the hooks 22, 22' or the holes 11, 11' can also provide an interference fit, thereby enhancing the tightness and robustness of the connection between the two. This can be particularly important if the bracket 20 is used as a handle to force the stimulator unit 10 into a tight periosteal pocket.

Figure 13:
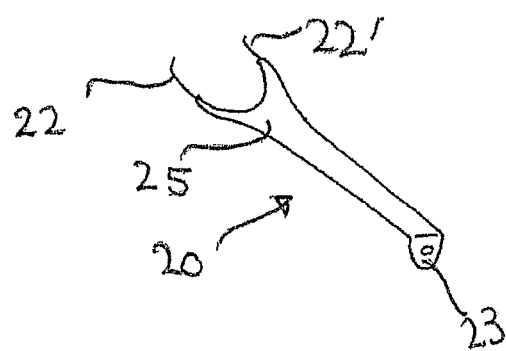
FIG. 13—shows an alternative form of the fixation connector according to the present invention.

A further alternative connecting arrangement between the bracket 20 and the stimulator unit 10 has the bracket 20 designed so as to connect with stimulator unit 10 underneath the unit. This configuration is shown in FIG. 13, where hooks or pins 22, 22' are turned upwards to be received in corresponding holes in stimulator unit 10 (not shown), disposed underneath the unit. In this view, the bracket 20 also has its shank bent to provide for a sagittal fixation at fixating point 23.

The bracket 20 also has a broader "plate" region 25 on which stimulator unit 10 will rest.

Figure 14:
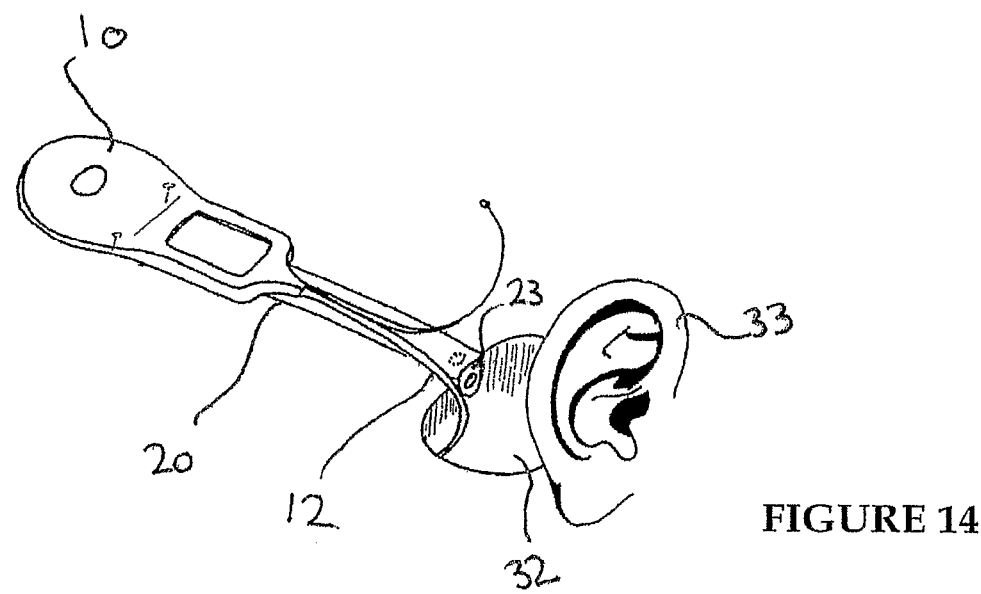
FIG. 14—shows the fixator connector of FIG. 13 in use.

FIG. 14 shows the bracket 20 of FIG. 13 connected with stimulator unit 10 from underneath, and in place on the patient's skull with connection point 23 being placed to fixate the arrangement sagitally in the patient's mastoid opening 32, underneath the pinna 33 of the outer ear.

Plate 25 (see FIG. 13) may be made from a mesh of biocompatible material to reduce the dead space and promote osseo-integration. Furthermore, because the bracket 20 in this configuration is between the stimulator unit 10 and the patient's skull, it could act as a slide to protect the stimulator unit when being inserted.

Figure 15:
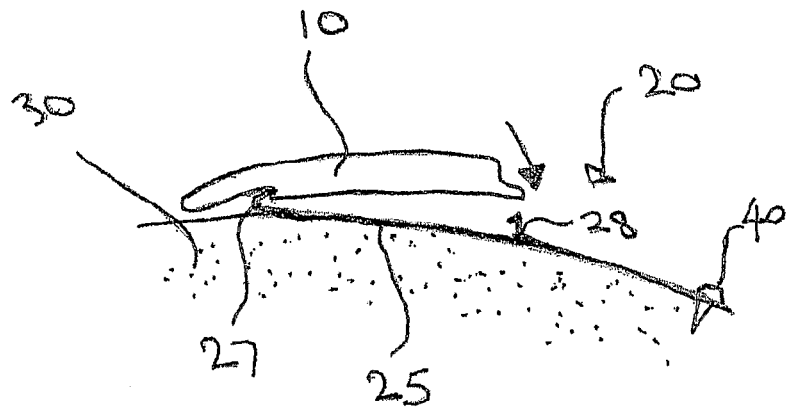
FIG. 15—shows a further modification of the fixation connector shown in FIG. 13, being used as a docking station.

A further modification of this aspect is to use the bracket 20 as a "docking station" for the implant. FIG. 15 shows bracket 20 being used as a docking station for stimulator unit 10. Bracket 20 in this case has been designed so that cradle 25 provides a docking bay with clips 27 and 28 to engage the stimulator unit 10. Of course, any other form of suitable engagement could be used.

As shown in FIG. 15, bracket 20 can be fixated to the patient's skull 30 as previously described, using bone screw 40 for example, and then stimulator unit 10 can be clipped or otherwise engaged with clips 27 and 28 to securely retain stimulator unit 10 in place.

Figure 16:
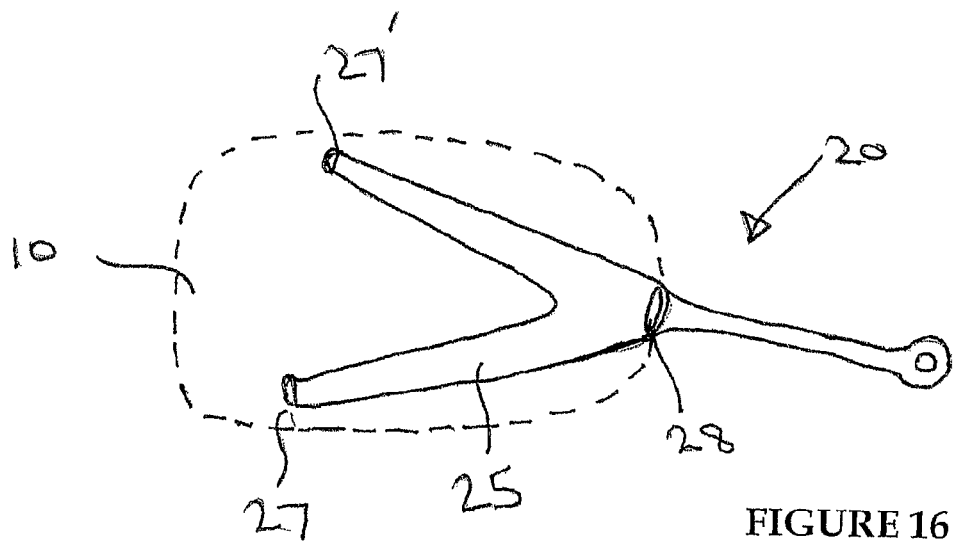
FIG. 16—is a top view of the fixation connector of FIG. 15.

FIG. 16 is a top view of bracket 20 of FIG. 15, showing clips 27, 27' and 28 for retaining stimulator unit 10 (shown in dotted lines this figure), which will rest in cradle 25 when in place. The configuration shown in FIG. 16 is but one of many possible configurations, and may again, be made from any suitable material or combination of materials. Cradle 25 may also be made of a wire frame to avoid or minimise dead spaces.

Figure 17:
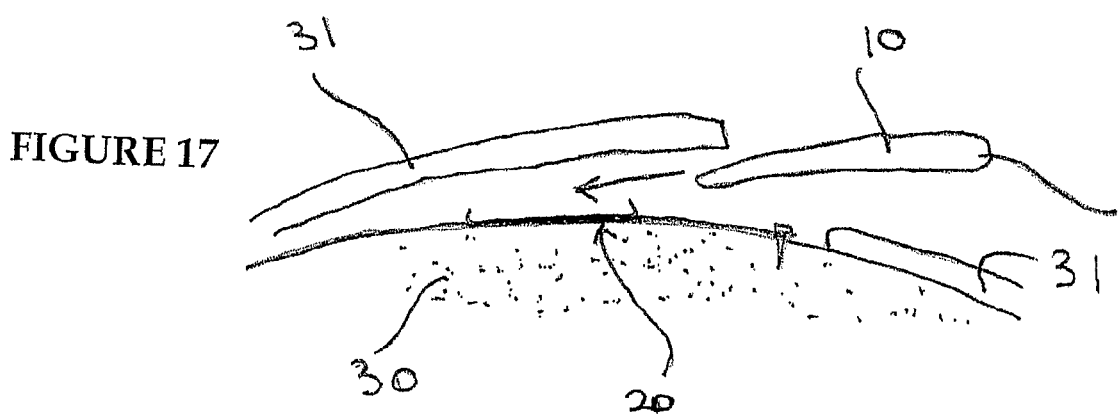
FIG. 17—shows the fixation connector of FIGS. 15 and 16 in use.

FIG. 17 shows a bracket 20 designed to act as a docking station fixated onto the patient's skull 30. As previously described, bracket 20 may be fixated to lie within a periosteal pocket under scalp 31. Stimulator unit 10 may then be slid into the pocket and clipped in secure engagement with bracket 20.

Of course it will be appreciated that the concept of the docking station need not be limited to a bracket having an extension for remote fixation of the bracket, and is equally applicable to a docking station that is fixated at the site of the implant.

According to another aspect of the present invention, the stimulator unit 10 could be provided with a series of "teeth" or sharp protrusions 13 on its lower face. These protrusions 13 would engage the bone to prevent or at least impede movement of the stimulator unit 10 once in place. When used in conjunction with bracket 20, the bracket could be used to hold the teeth away from the bone as the stimulator unit 10 is slid into place in its preferred location, and then when properly located, bracket 20 could then be lowered to lower stimulator unit 10 and its teeth into contact with the bone to allow engagement of the teeth with the skull. The teeth 13 could also promote osseo-integration.

Even if the stimulator unit 10 is placed with the aid of bracket 20, the existence of the teeth 13 may still impede the insertion of the implant, particularly if the stimulator unit 10 is required to be slid under a periosteal pocket along the mastoid bone. This aspect of the present invention therefore provides for a number of solutions to this problem as shown in FIGS. 18, 19 and 20.

Figure 18:
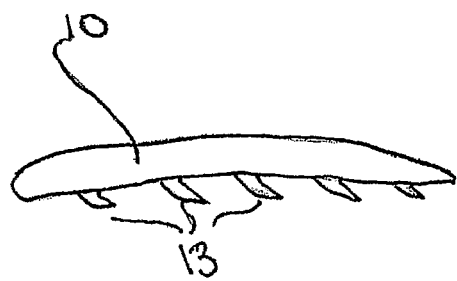
FIG. 18—shows a securing arrangement according to a different aspect of the present invention.

In FIG. 18, the teeth 13 are angled away from the insertion direction to facilitate sliding of the stimulator unit 10 into position. Once in position and teeth 13 have engaged the bone (not shown), the angle of teeth 13 makes it difficult for the stimulator unit 10 to have any anterior movement.

Figure 19:
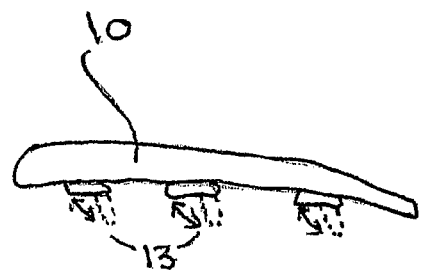
FIG. 19—shows an alternative to the arrangement of FIG. 18.

In FIG. 19, teeth 13 are provided by a series of folding spigots which can fold down into any depression or well drilled into the bone once in place.

Figure 20:
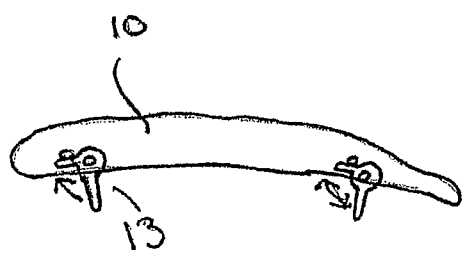
FIG. 20—shows a further alternative to the arrangement of FIG. 18.

FIG. 20 is an enhancement of the arrangement of FIG. 19 where the spigots have a winged member which engages with a stopper to allow movement in one direction only. In this case, the stimulator unit 10 may be slid into position with spigots lying flat against the unit. If the spigots pass over a well or depression in the bone, it drops down, but is unable to be raised again upon application of anterior movement to the stimulator unit 10.

Conceivably, the bracket 20 as illustrated in and discussed in reference to FIGS. 13 and 14 could have the plurality of protrusions incorporated underneath plate region 25. This allows standard stimulator units to be able to benefit from this aspect of the invention when used with such a modified bracket 20.

According to a further aspect of the present invention, bracket 20 may act as a guide and/or protector of the lead supporting the electrode array extending from stimulator unit 10.

Figure 21:
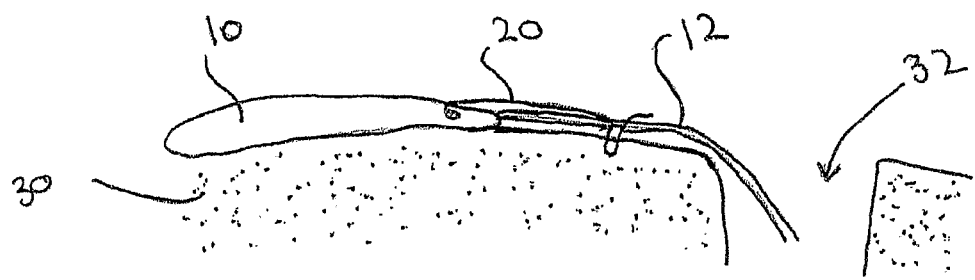
FIG. 21—shows a fixating connector according to a third aspect of the present invention.

FIG. 21 shows a stimulator unit 10 in place on bone 30 with lead 12 extending from stimulator unit 10 and into the mastoid opening 32. Lead 12 passes underneath bracket 20 and out through an opening at its end for feeding into the cochlear.

Figure 22:
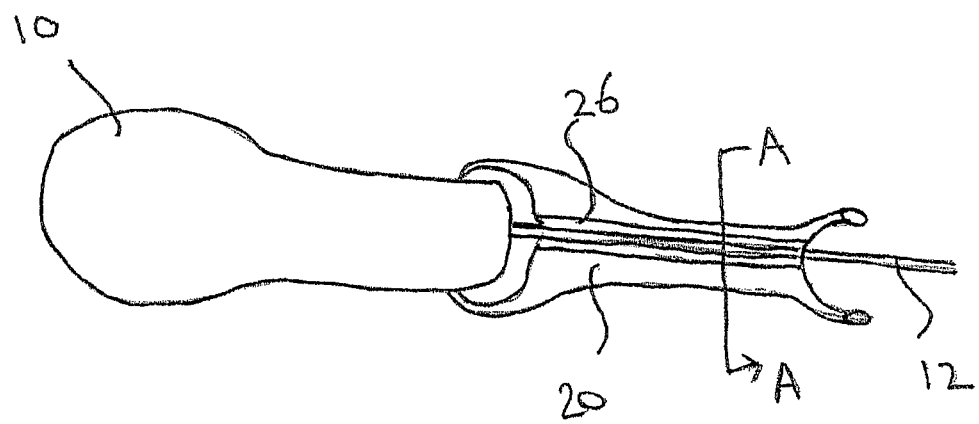
FIG. 22—shows a bottom view of the fixating connector of FIG. 21, in use.

FIG. 22 is a bottom view of the arrangement of FIG. 21. Shown here is the underneath of stimulator unit 10 connected to bracket 20 as previously described. Within the body of bracket 20 is formed a channel 26 which receives lead 12 along its length, until lead 12 exits bracket 20 and channel 26 at the end.

Figure 23:
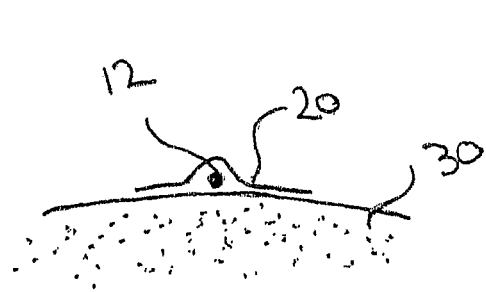
FIG. 23—shows a cross-sectional profile of the fixating connector of FIG. 21.

FIG. 23 is a cross-section of the arrangement of FIG. 22, along the line A-A, shown in location on skull 30. This shows that for at least a part of the length of lead 12, it is enclosed between skull 30 and bracket 20 within channel 26. The material of the bracket 20 may be a biocompatible mesh to again reduce the risk of infection in the space between the skull and the bracket 20.

Figure 24:
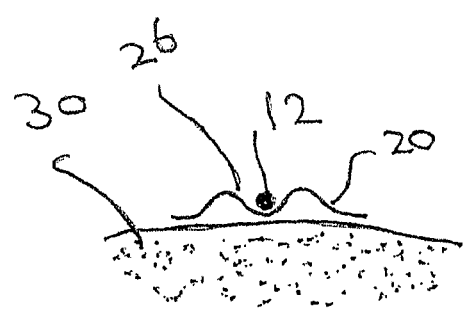
FIG. 24—shows a cross-sectional profile of an alternative arrangement of the fixating connector of FIG. 21.

FIG. 24 is a cross-section of an alternative configuration of bracket 20, this time formed to provide a channel 26 on the upward side of the bracket, away from skull 30. While not enclosing lead 12 completely, it does provide a guide and lateral protection.

The use of this aspect of the invention also reduces the likelihood of migration of the electrode array out of the cochlear.

It will be appreciated that this aspect of the invention encompasses a guide or protection member not necessarily provided by a bracket according to the first aspect of the invention. The guide or protecting member may be formed integral to the stimulator unit 10 or may also be provided as an attachment which does not necessarily also have to provide a fixation function.

It will be understood that the above has been described with reference to a particular embodiment and that many variations and modifications may be made to the invention without departing from the scopes of the various aspects of the present invention. For example, the fixating point may be provided as an integral extension of the implant to allow fixation of the implant remote from the implant.

It will also be understood that throughout this specification, unless the context requires otherwise, the words 'comprise' and 'include' and variations such as 'comprising' and 'including' will be understood to imply the inclusion of a stated integer or group of integers but not the exclusion of any other integer or group of integers.

The reference to any prior art in this specification is not, and should not be taken as, an acknowledgement or any form of suggestion that such prior art forms part of the common general knowledge.

The invention claimed is:

1. An implantable medical device comprising:
   an implantable unit configured to be implanted proximate bone of a recipient, the unit having first sides having respective faces that face directions approximately normal to a surface of the bone after implantation of the unit proximate bone; and
   a fixation bracket connected to the unit configured to fix the implantable medical device to the bone at a location remote from the implantable unit, wherein
   the bracket includes a fixating portion, a first portion and a second portion, the fixating portion being configured to be affixed to the bone at the remote location, a first end of the first portion extending from at least one of the first sides of the unit and a first end of the second portion extending from another of the first sides of the unit, second ends of the first and second portions being at least indirectly coupled to the fixating portion, and
   the bracket is sufficiently rigid to push the implantable unit in a direction of a force applied to the bracket.

2. The implantable medical device of claim 1, wherein:
   the bracket includes a connector configured to removably connect the bracket to the unit.

3. The implantable medical device of claim 2, wherein:
   the unit includes a hook receiver; and
   the connector is in the form of a hook that removably connects to the hook-receiver of the unit.

4. The implantable medical device of claim 1, wherein:
   the unit includes a plurality of bracket receivers; and
   the bracket includes unit interface portions that extend in directions about normal to a direction of extension of the first and second portions, respectively, the unit interface portions being configured to be received in respective bracket receivers, thereby removably connecting the bracket to the unit.

5. The implantable medical device of claim 4, wherein:
the first and second portions comprise respective elongate sub-portions having a length substantially longer than a maximum width of the first and second portions, the width lying in a plane normal to the direction of extension.

6. The implantable medical device of claim 1, wherein:
the bracket is configured to be detached from the unit via a single action consisting of movement of at least a given portion of the bracket relative to the unit.

7. The implantable medical device of claim 1, wherein:
the first and second portions splay away from one another from a location at about the remote location.

8. The implantable medical device of claim 1, wherein:
the implantable medical device includes only one fixating portion remote from the unit.

9. The implantable medical device of claim 1, wherein:
the implantable unit is a stimulator unit.

10. The implantable medical device of claim 9, wherein:
the stimulator unit is configured as a cochlear implant type of stimulator unit.

11. An implantable medical device comprising:
an implantable unit configured to be implanted proximate bone of a recipient, the unit having first sides having respective faces that face directions approximately normal to a surface of the bone after implantation of the unit proximate bone; and
a fixation bracket connected to the unit configured to fix the implantable medical device to the bone at a location remote from the implantable unit, wherein
the bracket includes a fixating portion, a first portion and a second portion, the fixating portion being configured to be affixed to the bone at the remote location, a first end of the first portion extending from at least one of the first sides of the unit and a first end of the second portion extending from another of the first sides of the unit, second ends of the first and second portions being at least indirectly coupled to the fixating portion, and
the bracket is sufficiently rigid to push the implantable unit in a direction of a force applied to the bracket, and
the bracket is generally at least one of wish-bone or "Y" shaped, the first and second portions corresponding to two of the extensions of wish-bone or "Y" shapes.

12. The implantable medical device of claim 11, wherein:
the implantable unit is a stimulator unit.

13. The implantable medical device of claim 12, wherein:
the stimulator unit is configured as a cochlear implant type of stimulator unit.

14. An implantable medical device, comprising:
a functional component hermetically sealed in a casing; and
a substantially rigid bracket attached to the casing, wherein
the casing has a length and a width that are both greater than a height of the casing,
the bracket includes a fixation component configured to be fixed to a skull of the recipient, the fixation component being located at a distance from the casing that is at least about half the distance of the length or the width of the casing, whichever is longer.

15. The implantable medical device of claim 14, wherein:
the length of the casing is longer than the width of the casing; and
the bracket extends from the casing in a direction of extension of the length of the casing.

16. The implantable medical device of claim 14, wherein:
the fixation component includes a hole configured to receive a bone screw.

17. The implantable medical device of claim 14, wherein:
the bracket is generally at least one of wish-bone and "Y" shaped.

* * * * *